US012661485B2

(12) United States Patent
Maeda et al.

(10) Patent No.: US 12,661,485 B2
(45) Date of Patent: Jun. 23, 2026

(54) GUIDE WIRE WITH TAPERED CORE AT THE DISTAL TIP PORTION HAVING VARIOUS COIL BODY TO PROVIDE VARYING STIFFNESS

(71) Applicant: Asahi Intecc Co., Ltd., Seto (JP)

(72) Inventors: Aoi Maeda, Seto (JP); Kenta Tsuge, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 338 days.

(21) Appl. No.: 18/210,083

(22) Filed: Jun. 15, 2023

(65) Prior Publication Data

US 2023/0321409 A1 Oct. 12, 2023

Related U.S. Application Data

(63) Continuation of application No. PCT/JP2020/048057, filed on Dec. 22, 2020.

(51) Int. Cl.
*A61M 25/09* (2006.01)
(52) U.S. Cl.
CPC ... *A61M 25/09* (2013.01); *A61M 2025/09083* (2013.01); *A61M 2025/09133* (2013.01); *A61M 2025/09191* (2013.01)
(58) Field of Classification Search
CPC ........ A61M 25/09; A61M 2025/09083; A61M 2025/09133; A61M 2025/09191; A61M 2025/0915; A61M 2025/09166
See application file for complete search history.

(56) References Cited

U.S. PATENT DOCUMENTS

| | | |
|---|---|---|
| 2010/0318065 A1 | 12/2010 | Miyata et al. |
| 2016/0001048 A1 | 1/2016 | Koike |
| 2021/0000421 A1* | 1/2021 | Sawai ................... A61B 5/0215 |

FOREIGN PATENT DOCUMENTS

| | | |
|---|---|---|
| JP | 2011-000188 A | 1/2011 |
| JP | 2011-143077 A | 7/2011 |
| JP | 2012-070853 A | 4/2012 |
| JP | 2012-135383 A | 7/2012 |
| JP | 5709224 B2 | 4/2015 |
| JP | 2016-013269 A | 1/2016 |

OTHER PUBLICATIONS

International Search Report and Written Opinion mailed on Jan. 26, 2021, received for PCT Application PCT/JP2020/048057, filed on Dec. 22, 2020, 9 pages including English Translation.

* cited by examiner

*Primary Examiner* — Serkan Akar
(74) *Attorney, Agent, or Firm* — XSENSUS LLP

(57) ABSTRACT

A guide wire includes a core shaft having an elongated outer shape, a first coil body disposed to surround a distal end portion of the core shaft, a second coil body disposed radially outside from the first coil body, and a distal tip fixing a distal end of the core shaft and a distal end of the first coil body. In the longitudinal direction of the core shaft, a distal end of the second coil body is positioned between the distal end of the first coil body and a proximal end of the first coil body, a proximal end of the second coil body is positioned on the more proximal end side than the proximal end of the first coil body, and bending stiffness of the first coil body is smaller than bending stiffness of the second coil body.

17 Claims, 15 Drawing Sheets

Fig. 7

GUIDE WIRE WITH TAPERED CORE AT THE DISTAL TIP PORTION HAVING VARIOUS COIL BODY TO PROVIDE VARYING STIFFNESS

CROSS-REFERENCE TO RELATED APPLICATION

This application is a continuation application of International Application No. PCT/JP2020/048057 filed Dec. 22, 2020, the entire contents of which is incorporated herein by reference.

TECHNICAL FIELD

The disclosed embodiments relate to a guide wire.

BACKGROUND ART

A guide wire used when a medical device such as a catheter is inserted into a blood vessel, digestive organ, or the like is known. For example, Patent Literature 1 discloses a guide wire in which a coil (hereinafter, also referred to as a "coil body") is attached to a distal end portion of a core wire (hereinafter, also referred to as a "core shaft") having an elongated shape, and the core wire and the coil are fixed with a brazing material. In the guide wire of Patent Literature 1, the coil is provided with: a tightly-winding portion in which adjacent strands are in close contact with each other; and a pitch opening portion in which adjacent strands are separated from each other, thereby preventing the brazing material from flowing during brazing, and maintaining flexibility of the distal end portion.

CITATION LIST

Patent Literature

Patent Literature 1: JP 2011-143077 A

SUMMARY

Technical Problems

Here, the guide wire advances inside a curved blood vessel while passing through a constricted or occluded lesion. Therefore, the distal end side of the guide wire may be bent into a U shape in response to resistance from the lesion or a blood vessel inner wall. In this regard, the guide wire described in Patent Literature 1 has a problem in which the bending of the guide wire on the distal end side may spread (extend) to the proximal end portion when the guide wire is further pushed forward in the state where the distal end side of the guide wire is bent. Such a problem is common to all guide wires inserted into organism lumens such as the lymph gland system, bile tract system, urinary system, respiratory tract system, digestive organ system, secreting gland system, and reproductive organs besides the blood vascular system.

The disclosed embodiments have been made in order to solve at least part of the above-described and other problems, and to provide a guide wire in which safeness is improved by preventing the bending caused on the distal end side of the guide wire from spreading (extending) to the proximal end side.

Solutions to Problems

The disclosed embodiments have been made in order to solve at least part of the above-described problem and other problems, and can be embodied as the following aspects.

(1) According to one aspect of the disclosed embodiments, a guide wire is provided. This guide wire includes a core shaft having an elongated outer shape, a first coil body disposed to surround a distal end portion of the core shaft, a second coil body disposed radially outside from the first coil body, and a distal tip fixing a distal end of the core shaft and a distal end of the first coil body, in which, in the longitudinal direction of the core shaft, a distal end of the second coil body is positioned between the distal end of the first coil body and a proximal end of the first coil body, a proximal end of the second coil body is positioned on the more proximal end side than the proximal end of the first coil body, and bending stiffness of the first coil body is smaller than bending stiffness of the second coil body.

According to this configuration, in the longitudinal direction of the core shaft, the distal end of the second coil body is positioned between the distal end of the first coil body and the proximal end of the first coil body, and the proximal end of the second coil body is positioned on the more proximal end side than the proximal end of the first coil body. As a result, the guide wire is configured to have, from the distal end side toward the proximal end side, a region (hereinafter, also referred to as a "first region") in which the core shaft is surrounded by the first coil body, and a region (hereinafter, also referred to as a "second region") in which the core shaft is surrounded by the first coil body and the second coil body. Here, according to this configuration, since the bending stiffness of the first coil body is smaller than the bending stiffness of the second coil body, the bending stiffness in the first region located on the distal end side is smaller than the bending stiffness in the second region. As a result, when the distal end portion of the guide wire receives resistance from a lesion or a blood vessel inner wall, bending caused in the guide wire is made possible to be readily caused within the first region and at the boundary between the first region and the second region. In addition, the bending caused in the distal end portion of the guide wire can be prevented from spreading (extending) to the second region located on the proximal end side. Accordingly, according to this configuration, safeness of the guide wire can be improved.

(2) The guide wire according to the above-described aspect may further include a first fixing portion fixing a distal end portion of the second coil body and a portion of the first coil body.

According to this configuration, since the guide wire includes the first fixing portion fixing the distal end portion of the second coil body and a portion of the first coil body, torquability (performance of transmitting, to the distal end side, an operation to the guide wire in a handheld portion) of the guide wire can be improved. In addition, since the first fixing portion is provided, bending caused in the guide wire is made possible to be readily caused on the more distal end side than the first fixing portion. As a result, the bending caused in the distal end portion of the guide wire can be further prevented from spreading to the second region located on the proximal end side.

(3) In the guide wire according to the above-described aspect, the first fixing portion may further fix the distal end portion of the second coil body and a portion of the core shaft.

According to this configuration, the first fixing portion further fixes the distal end portion of the second coil body and a portion of the core shaft. Hence, bending caused in the guide wire is made possible to be readily caused on the more distal end side than the first fixing portion, and the bending caused in the distal end portion of the guide wire can be further prevented from spreading to the second region located on the proximal end side.

(4) In the guide wire according to the above-described aspect, the core shaft may have: a tapered portion in which an outer diameter is thinned from a proximal end to a distal end; and a flat plate portion that is provided on the more distal end side than the tapered portion and has a flat plate outer shape, in which a proximal end of the flat plate portion may coincide with the distal end of the second coil body in terms of position in the longitudinal direction of the core shaft.

According to this configuration, since the core shaft has the flat plate portion that has a flat plate outer shape on the more distal end side than the tapered portion, shaping properties (properties indicating ease of imparting a shape when a shape such as a curved shape is imparted to the distal end portion of the guide wire in order to guide the distal end portion of the guide wire to a target blood vessel) of the guide wire can be improved. In addition, since the core shaft has the tapered portion in which the outer diameter thereof is thinned from the proximal end to the distal end, the distal end side of the guide wire can be made flexible. Furthermore, since the proximal end of the flat plate portion coincides with the distal end of the second coil body in terms of position in the longitudinal direction of the core shaft, difference in stiffness between the first region and the second region can be increased. As a result, bending caused in the guide wire is made possible to be further readily caused within the first region and at the boundary between the first region and the second region, and the bending caused in the distal end portion of the guide wire is further prevented from spreading to the second region located on the proximal end side. Accordingly, according to this configuration, safeness of the guide wire can be further improved, and usability of the guide wire can be improved.

(5) The guide wire according to the above-described aspect may further include a tubular body disposed radially outside from the second coil body, in which a proximal end of the tubular body is positioned on the more proximal end side than the proximal end of the second coil body, and the distal tip may further fix a distal end of the tubular body.

According to this configuration, since the proximal end of the tubular body is positioned on the more proximal end side than the proximal end of the second coil body, a region (hereinafter, also referred to as a "third region") in which the core shaft is surrounded by the tubular body on the proximal end side of the second region can be formed.

(6) The guide wire according to the above-described aspect may further include a second fixing portion fixing a portion of the core shaft, a portion of the first coil body, a portion of the second coil body, and a portion of the tubular body.

According to this configuration, since the guide wire includes the second fixing portion fixing a portion of the core shaft, a portion of the first coil body, a portion of the second coil body, and a portion of the tubular body, torquability of the guide wire can be improved. In addition, since the first coil body, the second coil body, and the tubular body are fixed to the core shaft by the second fixing portion, positions of the first coil body, the second coil body, and the tubular body can be prevented from moving in the longitudinal direction (in other words, the first coil body, the second coil body, and the tubular body can be prevented from displacing from one another).

(7) The guide wire according to the above-described aspect may further include a coating layer coating outer surfaces of the distal tip, the tubular body, and the core shaft positioned on the more proximal end side than the tubular body.

According to this configuration, since the guide wire includes the coating layer coating the outer surfaces of the distal tip, the tubular body, and the core shaft positioned on the more proximal end side than the tubular body, slidability of the guide wire inside a blood vessel can be improved.

Incidentally, the disclosed embodiments can be embodied in various aspects and can be embodied in forms of a guide wire and a set of a coil body and a tubular body attached to a guide wire, and in a form of a production method therefore, for example.

BRIEF DESCRIPTION OF DRAWINGS

FIG. 7 is a diagram illustrating an example of a configuration of a guide wire according to a third embodiment.

DETAILED DESCRIPTION

First Embodiment

Figure 1:
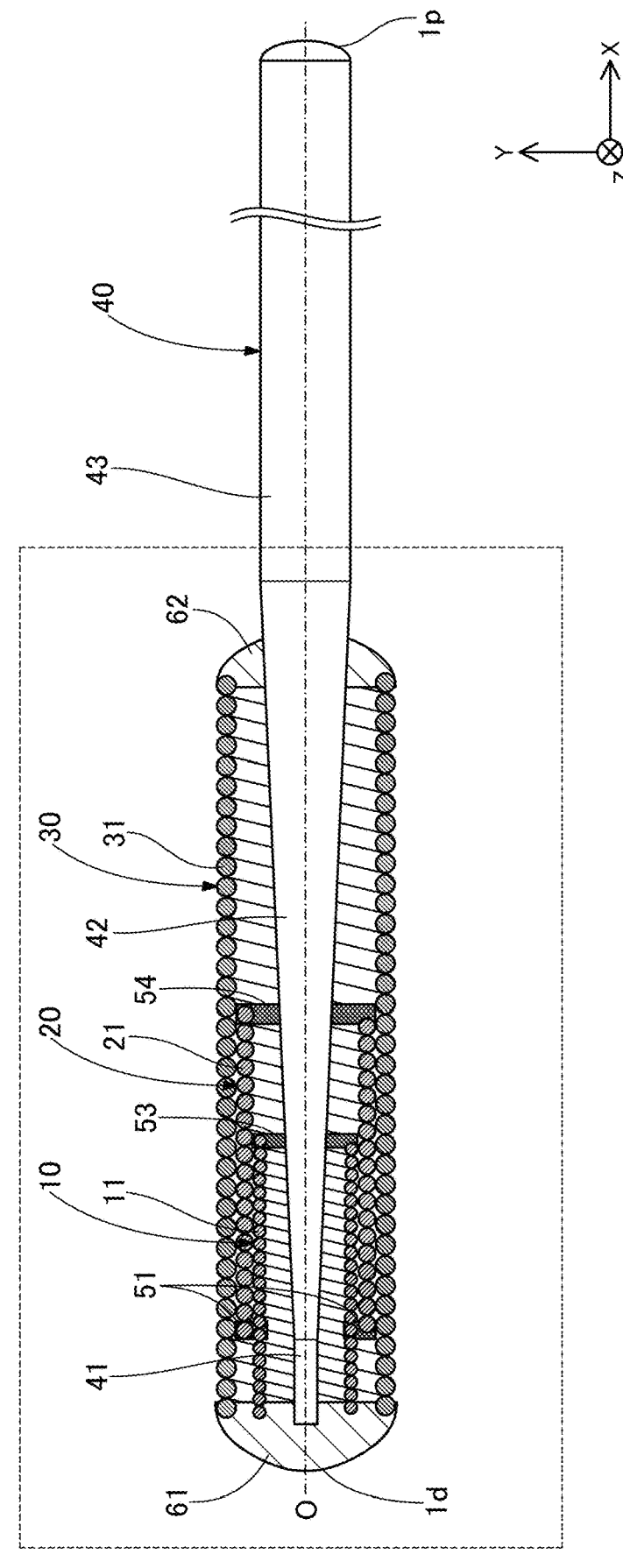
FIG. 1 is a diagram illustrating an example of a configuration of a guide wire according to a first embodiment.

FIG. 1 is a diagram illustrating an example of a configuration of a guide wire 1 according to a first embodiment. The guide wire 1 is a medical tool used when a medical device such as a catheter is inserted into a blood vessel or the like. The guide wire 1 includes a first coil body 10, a second coil body 20, a third coil body 30, a core shaft 40, a first fixing portion 51, a third fixing portion 53, a fourth fixing portion 54, a distal tip 61, and a proximal end side fixing portion 62. As used herein, "fixing portion" includes any appropriate mechanism for securing components together. The guide wire 1 has the configuration described below; consequently, when a distal end portion of the guide wire 1 receives resistance from a lesion or a blood vessel inner wall inside a blood vessel, bending caused in the guide wire 1 is prevented from spreading (extending) to the proximal end side, and safeness can be improved. Incidentally, although explanation will be made with a blood vessel as an example in the following examples, the guide wire 1 can be inserted into organism lumens such as the lymph gland system, bile tract system, urinary system, respiratory tract system, digestive organ system, secreting gland system, and reproductive organs besides the blood vascular system and used.

In FIG. 1, an axis passing through the center of the guide wire 1 is represented by an axis line O (dash-dot-dash line). In the example illustrated in FIG. 1, the axis line O coincides with axes respectively passing through the first to third coil bodies 10, 20, 30 and the core shaft 40. However, the axis line O may deviate from the central axes of the respective constituting members described above. FIG. 1 shows X-, Y-, and Z-axes orthogonal to one another. The X-axis corresponds to the longitudinal direction of the guide wire 1, the Y-axis corresponds to the height direction of the guide wire 1, and the Z-axis corresponds to the width direction of the guide wire 1. The left side (−X-axis direction) in FIG. 1 is referred to as the "distal end side" of each of the guide wire 1 and the constituting members, and the right side (+X-axis direction) in FIG. 1 is referred to as the "proximal end side" of each of the guide wire 1 and the constituting members. In addition, one end positioned on the distal end side of the both ends in the longitudinal direction (X-axis direction) of each of the guide wire 1 and the constituting members is referred to as the "distal end," and the other end positioned on the proximal end side is referred to as the "proximal end." Furthermore, the distal end and the vicinity thereof are referred to as the "distal end portion," and the proximal end and the vicinity thereof are referred to as the "proximal end portion." The distal end side is inserted into the inside of a living body, and the proximal end side is operated by an operator such as a medical doctor. These points are also true for figures following FIG. 1.

Figure 2:
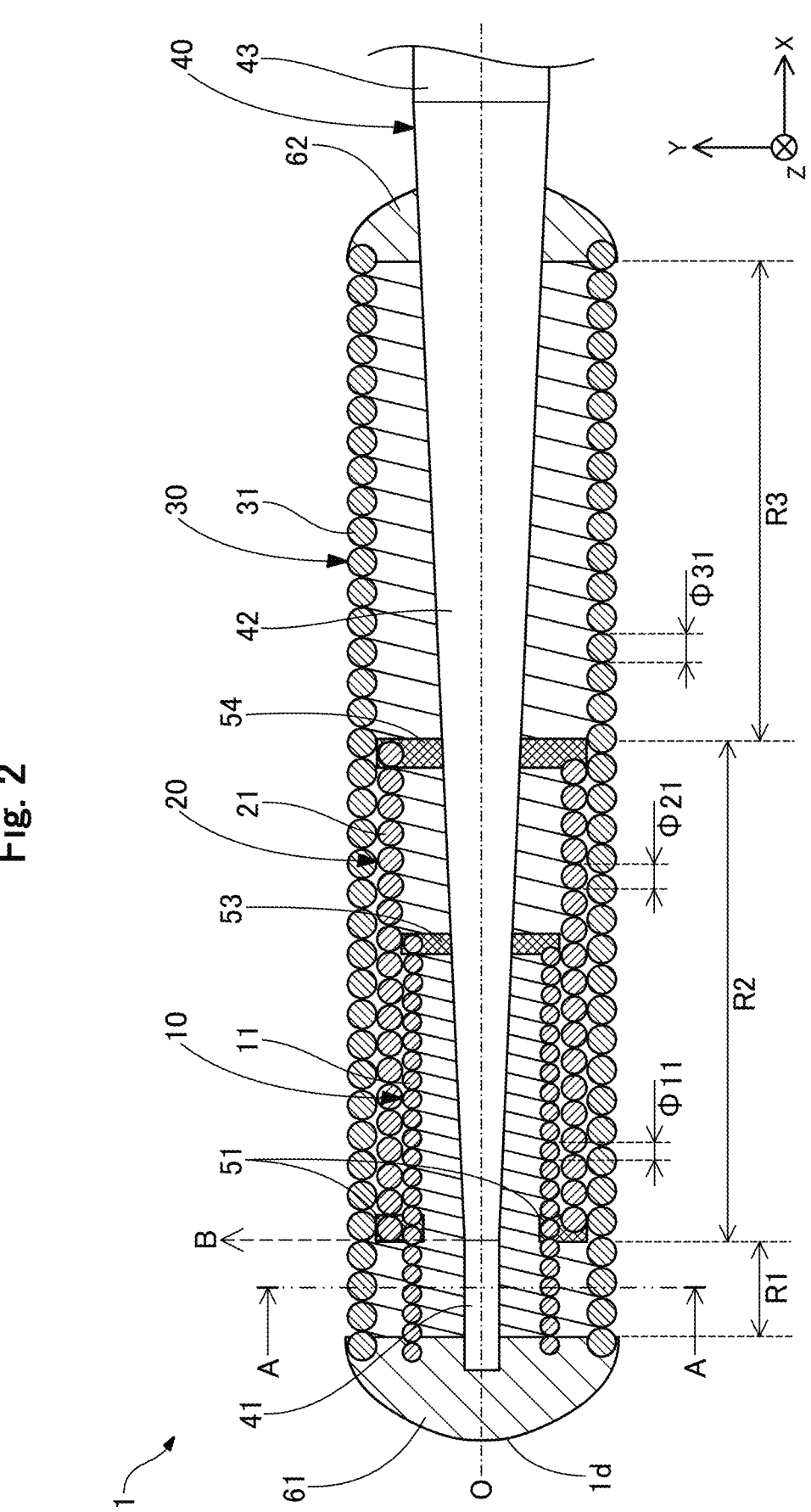
FIG. 2 is an enlarged view illustrating a portion (FIG. 1: within the frame drawn with a dashed line) on the distal end side of the guide wire.
Figure 3:
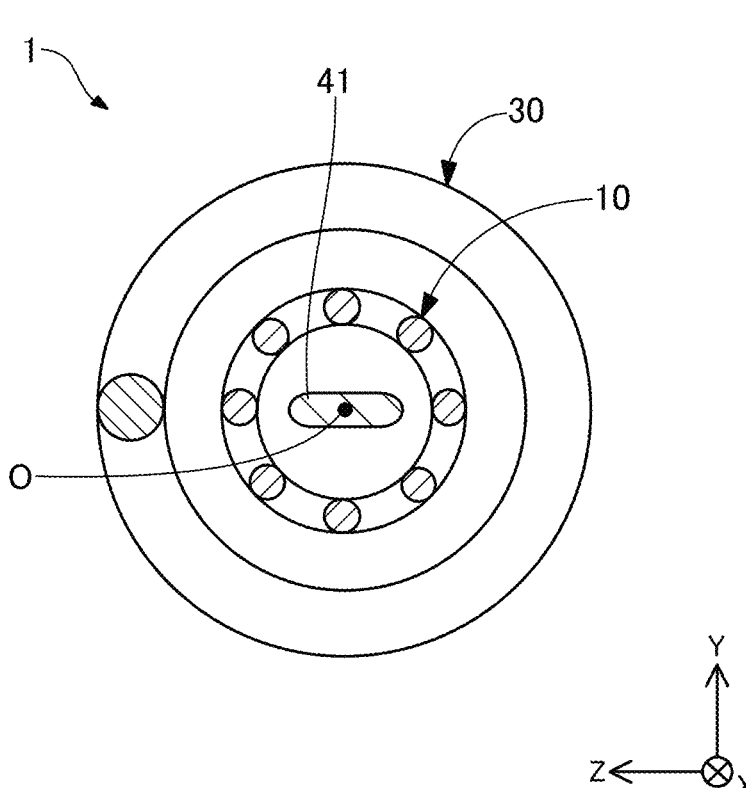
FIG. 3 is a diagram illustrating an example of a cross-sectional configuration along the line A-A in FIG. 2.

FIG. 2 is an enlarged view illustrating a portion (FIG. 1: within the frame drawn with a dashed line) on the distal end side of the guide wire 1. FIG. 3 is a diagram illustrating an example of a cross-sectional configuration along the line A-A in FIG. 2. As illustrated in FIG. 1, the core shaft 40 has an elongated outer shape extending along the axis line O. The core shaft 40 has a flat plate portion 41, a tapered portion 42, and a large-diameter portion 43 from the distal end to the proximal end.

The flat plate portion 41 is disposed on the most distal end side of the core shaft 40. The flat plate portion 41 has an elongated shape extending coaxially with the axis line O of the guide wire 1 (FIG. 1, FIG. 2), and is a portion having a flat plate outer shape in which the length in the Y-axis direction is shorter than the length in the Z-axis direction in the cross-section illustrated in FIG. 3. As illustrated in FIG. 2, the distal end of the flat plate portion 41 is fixed by the distal tip 61 to the first coil body 10 and the third coil body 30. The tapered portion 42 is connected to the proximal end of the flat plate portion 41. In addition, as illustrated in FIG. 2, the position B of the proximal end of the flat plate portion 41 coincides with the position B of the distal end of the second coil body 20, in the axis line O direction (in other words, the longitudinal direction of the core shaft 40) such that the distal end of the second coil body and the proximal end of the flat plate portion 41 are aligned along the longitudinal direction. Incidentally, in the present embodiment, the terms "coincident" and "aligned" means an approximately coincident or aligned state and allows differences due to manufacturing errors and the like.

The flat plate portion 41 is a member for facilitating impartment of a shape, when an operator imparts a shape such as a curved shape to the distal end portion of the guide wire 1, and is also referred to as a "ribbon." Incidentally, the outer diameters (the lengths in the Y-axis direction and the Z-axis direction in FIG. 3), the length in the axis line O direction, and the cross-sectional shape of the flat plate portion 41 can be arbitrarily determined. The flat plate portion 41 may not be coaxial with the tapered portion 42 and the large-diameter portion 43. In this case, one side surface on the proximal end side of the flat plate portion 41 may be joined to one side surface on the distal end side of the tapered portion 42. In addition, the flat plate portion 41 may be omitted.

As illustrated in FIG. 1, the tapered portion 42 is disposed between the flat plate portion 41 and the large-diameter portion 43. The tapered portion 42 is a portion having an approximately truncated cone shape in which the outer diameter is reduced from the proximal end to the distal end. As illustrated in FIG. 2, the flat plate portion 41 is connected to the distal end of the tapered portion 42, and the large-diameter portion 43 is connected to the proximal end of the tapered portion 42. Incidentally, the outer diameter, the length in the axis line O direction, and the cross-sectional shape of the tapered portion 42 can be arbitrarily determined.

The large-diameter portion 43 is disposed on the most proximal end side of the core shaft 40. The large-diameter portion 43 is a portion having an approximately columnar shape in which the outer diameter is approximately constant from the proximal end to the distal end. The outer diameter of the large-diameter portion 43 is identical to that of a portion of the tapered portion 42 having the largest diameter. Incidentally, in the present embodiment, the term "identical" means being approximately identical and allows differences due to manufacturing errors and the like. As illustrated in FIG. 2, the tapered portion 42 is connected to the distal end of the large-diameter portion 43. The proximal end portion of the large-diameter portion 43 is held by an operator and operated. Incidentally, the outer diameter, the length in the axis line O direction, and the cross-sectional shape of the large-diameter portion 43 can be arbitrarily determined.

The core shaft 40 may be formed from a superelastic alloy (also referred to as a "pseudoelastic alloy"). Examples of the superelastic alloy include NiTi alloys and alloys of NiTi and another metal. Incidentally, the flat plate portion 41 of the core shaft 40 may be formed from a material which is more likely than superelastic alloys to be plastically deformed. Examples of the material which is more likely than superelastic alloys to be plastically deformed include stainless steel alloys such as SUS304 and SUS316. In addition, a hand side core shaft may be further provided on the more proximal end side than the large-diameter portion 43. The hand side core shaft may be formed from a material which is more likely than superelastic alloys to be plastically deformed, for example.

As illustrated in FIG. 2, the first coil body 10 surrounds the distal end portion of the core shaft 40. Specifically, the first coil body 10 surrounds the flat plate portion 41 and a portion of the tapered portion 42 on the distal end side. The distal end of the first coil body 10 is fixed to the core shaft

40 and the third coil body 30 by the distal tip 61. The proximal end of the first coil body 10 is fixed to the core shaft 40 by the third fixing portion 53. Incidentally, the average coil diameter of the first coil body 10 (the average diameter of the outer diameter and the inner diameter of the first coil body 10) and the length of the first coil body 10 can be arbitrarily determined.

Figure 4:
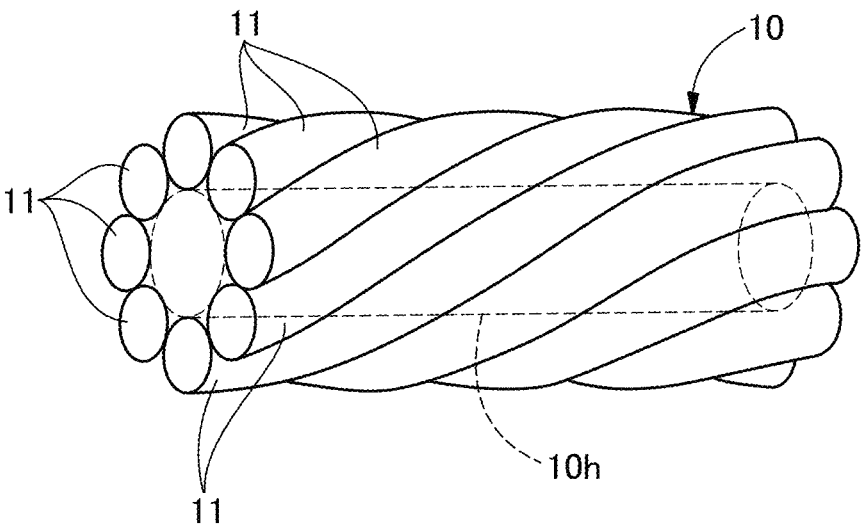
FIG. 4 is a perspective view illustrating an example of a configuration of a first coil body.

FIG. 4 is a perspective view illustrating an example of a configuration of the first coil body 10. As illustrated in FIG. 4, the first coil body 10 according to the present embodiment is a multi-thread coil in which eight strands 11 are wound in a multi-thread manner and has an approximately cylindrical shape having a constant outer diameter. The first coil body 10 can be formed by, for example, tightly twisting the eight strands 11 on a core metal so as to be in contact with each other, subsequently removing residual stress using a known heat treatment method, and extracting the core metal. The first coil body 10 formed in such a manner is a multi-thread coil having an inner cavity 10h (dashed line) as illustrated in FIG. 4. The material for the strands 11 may be the same as or different from the material for strands 21. Incidentally, any forms can be employed on the first coil body 10, and the number of strands 11 constituting the first coil body 10 is not limited to eight and may be arbitrarily determined, for example. The first coil body 10 is not limited to a multi-thread coil, may be a single thread coil formed by winding one strand in a single thread manner, may be a single thread twisted coil formed by winding, in a single thread manner, a twisted wire in which a plurality of strands are twisted, and may be a multi-thread twisted coil formed by winding twisted wires in a multi-thread manner using multiple twisted wires each obtained by twisting a plurality of strands.

As illustrated in FIG. 2, the second coil body 20 is disposed on the radially outer side of the first coil body 10 and surrounds a portion of the core shaft 40 (in the example illustrated in the figure, a portion of the tapered portion 42 on the distal end side) and a portion of the first coil body 10 on the proximal end side. The distal end of the second coil body 20 is positioned between the distal end of the first coil body 10 and the proximal end of the first coil body 10 in the axis line O direction (in other words, the longitudinal direction of the core shaft 40). The distal end of the second coil body 20 is fixed to the first coil body 10 by the first fixing portion 51. In addition, the proximal end of the second coil body 20 is positioned on the more proximal end side than the proximal end of the first coil body 10 in the axis line O direction. The proximal end of the second coil body 20 is fixed to the core shaft 40 by the fourth fixing portion 54.

The second coil body 20 is a multi-thread coil in which multiple (for example, eight) strands 21 are wound in a multi-thread manner as with the first coil body 10 described with reference to FIG. 4; however, the second coil body 20 is not limited to a multi-thread coil and may be a single thread coil, may be a single thread twisted coil, and may be a multi-thread twisted coil. Incidentally, the average coil diameter of the second coil body 20 (the average diameter of the outer diameter and the inner diameter of the second coil body 20) and the length of the second coil body 20 can be arbitrarily determined.

The third coil body 30 is disposed on the radially outer side of the second coil body 20 and surrounds a portion of the core shaft 40 (in the example illustrated in the figure, the flat plate portion 41 and a portion of the tapered portion 42 on the distal end side), the first coil body 10, and the second coil body 20. The distal end of the third coil body 30 is located at the same position as the distal end of the first coil body 10 in the axis line O direction. The distal end of the third coil body 30 is fixed to the core shaft 40 and the first coil body 10 by the distal tip 61. In addition, the proximal end of the third coil body 30 is positioned on the more proximal end side than the proximal end of the second coil body 20 in the axis line O direction. The proximal end of the third coil body 30 is fixed to the core shaft 40 by the proximal end side fixing portion 62.

The third coil body 30 is a single thread coil formed by winding one strand in a single thread manner. However, the third coil body 30 is not limited to a single thread coil and may be a multi-thread coil, may be a single thread twisted coil, and may be a multi-thread twisted coil. Incidentally, the average coil diameter of the third coil body 30 (the average diameter of the outer diameter and the inner diameter of the third coil body 30) and the length of the third coil body 30 can be arbitrarily determined. Here, the third coil body 30 corresponds to the "tubular body".

The strands 11 constituting the first coil body 10, the strands 21 constituting the second coil body 20, and the strand 31 constituting the third coil body 30 can be formed from an arbitrary material. The strands 11, the strands 21, and the strand 31 can be formed from, for example, a radiolucent alloy such as a stainless steel alloy including SUS304 and SUS316, a superelastic alloy including a NiTi alloy, a piano wire, a nickel-chromium-based alloy, and a cobalt alloy, gold, platinum, tungsten, and a radiopaque alloy such as an alloy including gold, platinum, or tungsten (for example, a platinum-nickel alloy). The strands 11, the strands 21, and the strand 31 may be formed from the same material or may be formed from different materials. In the present embodiment, the magnitude relationship between the outer diameter Ø11 of the strands 11, the outer diameter Ø21 of the strands 21, and the outer diameter Ø31 of the strand 31 satisfies the inequality expression Ø11<Ø21<Ø31. However, this magnitude relationship can be arbitrarily determined, and may be Ø11=Ø21<Ø31, and may be Ø11=Ø21=Ø31, for example.

Incidentally, in the present embodiment, the outer peripheral surface of the first coil body 10 and the inner peripheral surface of the second coil body 20 are in contact with each other, the outer peripheral surface of the second coil body 20 and the inner peripheral surface of the third coil body 30 are in contact with each other. However, the outer peripheral surface of the first coil body 10 and the inner peripheral surface of the second coil body 20 may be separated from each other, and the outer peripheral surface of the second coil body 20 and the inner peripheral surface of the third coil body 30 may be separated from each other.

The distal tip 61 is disposed at the distal end of the third coil body 30 and integrally holds the distal end of the third coil body 30, the distal end of the core shaft 40, and the distal end of the first coil body 10. The proximal end side fixing portion 62 is disposed at the proximal end of the third coil body 30 and integrally holds the proximal end of the third coil body 30 and a portion of the core shaft 40 (specifically, a portion of the tapered portion 42). The first fixing portion 51 is disposed at the distal end of the second coil body 20 and integrally holds the distal end of the second coil body 20 and a portion of the first coil body 10. The fourth fixing portion 54 is disposed at the proximal end of the second coil body 20 and integrally holds the proximal end of the second coil body 20 and a portion of the core shaft 40 (specifically, a portion of the tapered portion 42). The third fixing portion 53 is disposed at the proximal end of the first coil body 10 and integrally holds the proximal end of the first coil body 10 and a portion of the core shaft 40 (specifically, a portion of the tapered portion 42).

The distal tip 61, the proximal end side fixing portion 62, the first fixing portion 51, the third fixing portion 53, and the fourth fixing portion 54 can each be formed by means of an arbitrary bonding agent such as metal solder including silver solder, gold solder, zinc, Sn—Ag alloy, and Au—Sn alloy, or an adhesive including an epoxy-based adhesive. The distal tip 61, the proximal end side fixing portion 62, the first fixing portion 51, the third fixing portion 53, and the fourth fixing portion 54 may each be formed by using the same bonding agent, or may be formed by using a different bonding agent from one another. Incidentally, the distal tip 61, the proximal end side fixing portion 62, the first fixing portion 51, the third fixing portion 53, and the fourth fixing portion 54 may be formed by laser welding.

Figure 5A:
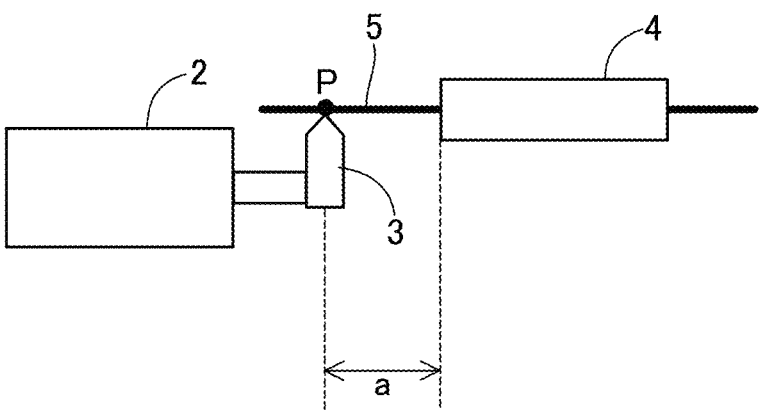
FIGS. 5A and 5B are diagrams illustrating an example of a method for measuring bending stiffness.
Figure 5B:
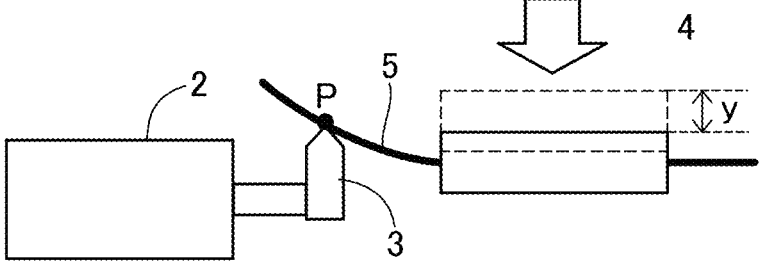

FIGS. 5A and 5B are diagrams illustrating an example of a method for measuring bending stiffness. The bending stiffness of the first coil body 10 is smaller than the bending stiffness of the second coil body 20 in the guide wire 1 described above. In the present embodiment, bending stiffness is measured by a cantilever test illustrated in FIGS. 5A and 5B. Specifically, as illustrated in FIG. 5A, a measuring object 5 is supported by a gripping tool 4. A load sensor 3 of a measuring device 2 is placed in contact with an arbitrary position of the measuring object 5 protruding from the gripping tool 4. At this time, a predetermined distance a is provided between the end face (end face on the side facing the measuring device 2) of the gripping tool 4 and the contact point P between the measuring object 5 and the load sensor 3. In this state, the gripping tool 4 is lowered in a predetermined amount with the contact point P as the power point, as illustrated in FIG. 5B. Then, the measurement value obtained from the load sensor 3 when the gripping tool 4 reaches a predetermined displacement amount y is taken as the bending stiffness of the measuring object 5. The bending stiffness of the first coil body 10 measured in this manner is smaller than the bending stiffness of the second coil body 20.

The guide wire 1 of the present embodiment has a first region R1, a second region R2, and a third region R3 from the distal end side toward the proximal end side, as illustrated in FIG. 2. The first region R1 is a region in which the core shaft 40 is surrounded by the first coil body 10. In the example illustrated in the drawing, the distal end of the first region R1 coincides with the position of the proximal end of the distal tip 61, and the proximal end of the first region R1 coincides with the position of the distal end of the second coil body 20, in the axis line O direction. The second region R2 is a region in which the core shaft 40 is surrounded by the first coil body 10 and the second coil body 20. In the example illustrated in the drawing, the distal end of the second region R2 coincides with the position of the distal end of the second coil body 20, and the proximal end of the second region R2 coincides with the position of the proximal end of the second coil body 20, in the axis line O direction. The third region R3 is a region in which the core shaft 40 is surrounded by the third coil body 30. In the example illustrated in the drawing, the distal end of the third region R3 coincides with the position of the proximal end of the second coil body 20, and the proximal end of the third region R3 coincides with the position of the distal end of the proximal end side fixing portion 62, in the axis line O direction.

As described with reference to FIGS. 5A and 5B, the bending stiffness of the first coil body 10 is smaller than the bending stiffness of the second coil body 20. Therefore, the bending stiffness in the first region R1 of the guide wire 1 is smaller than the bending stiffness in the second region R2 (bending stiffness: first region R1<second region R2). In addition, as the tapered portion 42 extending from the second region R2 to the third region R3 is gradually thickened from the distal end side to the proximal end side, the stiffness thereof gradually increases. Consequently, the bending stiffness in the second region R2 of the guide wire 1 is smaller than the bending stiffness in the third region R3 (bending stiffness: second region R2<third region R3). As described above, the bending stiffness of the guide wire 1 of the present embodiment is smallest in the first region R1 located on the most distal end side, and the bending stiffness increases in the order of the second region R2 and the third region R3. Incidentally, the bending stiffness in the second region R2 may be made equal to the bending stiffness in the third region R3 by adjusting the shape of the tapered portion 42 (bending stiffness: second region R2=third region R3).

As described above, according to the guide wire 1 of the first embodiment, the distal end of the second coil body 20 is disposed between the distal end of the first coil body 10 and the proximal end of the first coil body 10, and the proximal end of the second coil body 20 is positioned on the more proximal end side than the proximal end of the first coil body 10, in the longitudinal direction (axis line O direction) of the core shaft 40. As a result, the guide wire 1 is configured to have the first region and the second region described above from the distal end side toward the proximal end side. Here, since the bending stiffness of the first coil body 10 is smaller than the bending stiffness of the second coil body 20, the bending stiffness in first region R1 located on the distal end side is smaller than that in the second region R2. As a result, when the distal end portion of the guide wire 1 receives resistance from a lesion or a blood vessel inner wall, bending caused in the guide wire 1 is made possible to be readily caused within the first region R1 and at the boundary between the first region R1 and the second region R2. In addition, the bending caused in the distal end portion of the guide wire 1 can be prevented from spreading (extending) to the second region R2 located on the proximal end side. Accordingly, according to the guide wire 1 of the present embodiment, safeness can be improved.

In addition, since the guide wire 1 of the first embodiment includes the first fixing portion 51 fixing the distal end portion of the second coil body 20 and a portion of the first coil body 10, torquability (performance of transmitting, to the distal end side, an operation to the guide wire 1 in a handheld portion) of the guide wire 1 can be improved. In addition, by virtue of including the first fixing portion 51, bending caused in the guide wire 1 is made possible to be readily caused on the more distal end side than the first fixing portion 51. As a result, the bending caused in the distal end portion (that is, the first region R1) of the guide wire 1 can be further prevented from spreading to the second region R2 located on the proximal end side.

Furthermore, according to the guide wire 1 of the first embodiment, since the core shaft 40 has, on the more distal end side than the tapered portion 42, the flat plate portion 41 having a flat plate outer shape, shaping properties (properties indicating ease of imparting a shape when a shape such as a curved shape is imparted to the distal end portion of the guide wire 1 in order to guide the distal end portion of the guide wire 1 to a target blood vessel) of the guide wire 1 can be improved. In addition, since the core shaft 40 has the tapered portion 42 in which the outer diameter is thinned from the proximal end to the distal end, the distal end side of the guide wire 1 can be made flexible. Furthermore, since the proximal end of the flat plate portion 41 coincides with the distal end of the second coil body 20 in terms of position in the longitudinal direction of the core shaft 40 (FIG. 2: position B), difference in stiffness between the first region R1 and the second region R2 can be made larger. As a result, bending caused in the guide wire 1 is made possible to be further readily caused within the first region R1 and at the boundary between the first region R1 and the second region R2, and the bending caused in the distal end portion of the guide wire 1 is further prevented from spreading to the second region R2 located on the proximal end side. Accordingly, safeness of the guide wire 1 can be further improved, and usability of the guide wire 1 can be improved.

Furthermore, according to the guide wire 1 of the first embodiment, the first fixing portion 51 fixes the first coil body 10 and the second coil body 20 but does not fix the core shaft 40; therefore, the flexibility of the guide wire 1 can be maintained. Similarly, the third fixing portion 53 fixes the first coil body 10 and the core shaft 40 but does not fix the second coil body 20 and the third coil body 30; therefore, the flexibility of the guide wire 1 can be maintained. Similarly, the fourth fixing portion 54 fixes the second coil body 20 and the core shaft 40 but does not fix the third coil body 30; therefore, the flexibility of the guide wire 1 can be maintained.

Second Embodiment

Figure 6:
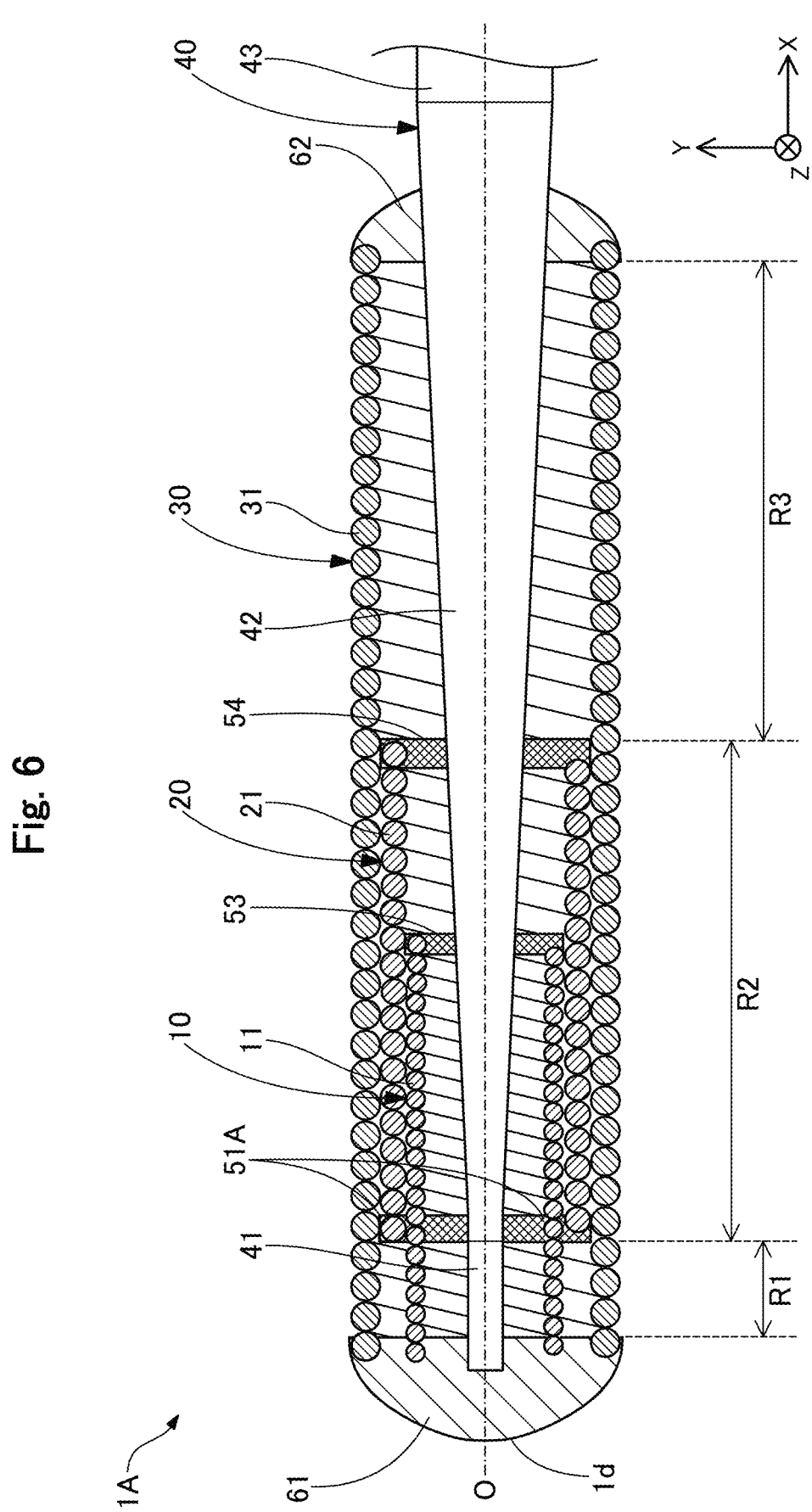
FIG. 6 is a diagram illustrating an example of a configuration of a guide wire according to a second embodiment.

FIG. 6 is a diagram illustrating an example of a configuration of a guide wire 1A according to a second embodiment. The guide wire 1A of the second embodiment includes a first fixing portion 51A instead of the first fixing portion 51 in the configuration described in the first embodiment. The first fixing portion 51A is disposed at the distal end of the second coil body 20, fixes a portion of the core shaft 40 (in the example illustrated in the drawing, the distal end portion of the tapered portion 42) in addition to the distal end of the second coil body 20 and a portion of the first coil body 10, and integrally holds same.

As such, the configuration of the guide wire 1A can be modified in various ways, and the first fixing portion 51A may fix the core shaft 40 besides the first coil body 10 and the second coil body 20. In addition, the first fixing portion 51A may further fix a portion of the third coil body 30 in addition to the distal end of the second coil body 20 and a portion of the first coil body 10. The same effect as in the first embodiment described above can be provided also by this guide wire 1A of the second embodiment. In addition, according to the guide wire 1A of the second embodiment, the first fixing portion 51A further fixes the distal end portion of the second coil body 20 and a portion of the core shaft 40. Consequently, bending caused in the guide wire 1A is made possible to be readily caused on the more distal end side (that is, the first region R1) than the first fixing portion 51A, and the bending caused in the distal end portion of the guide wire 1A can be further prevented from spreading to the second region R2 located on the proximal end side.

Third Embodiment

Figure 7:
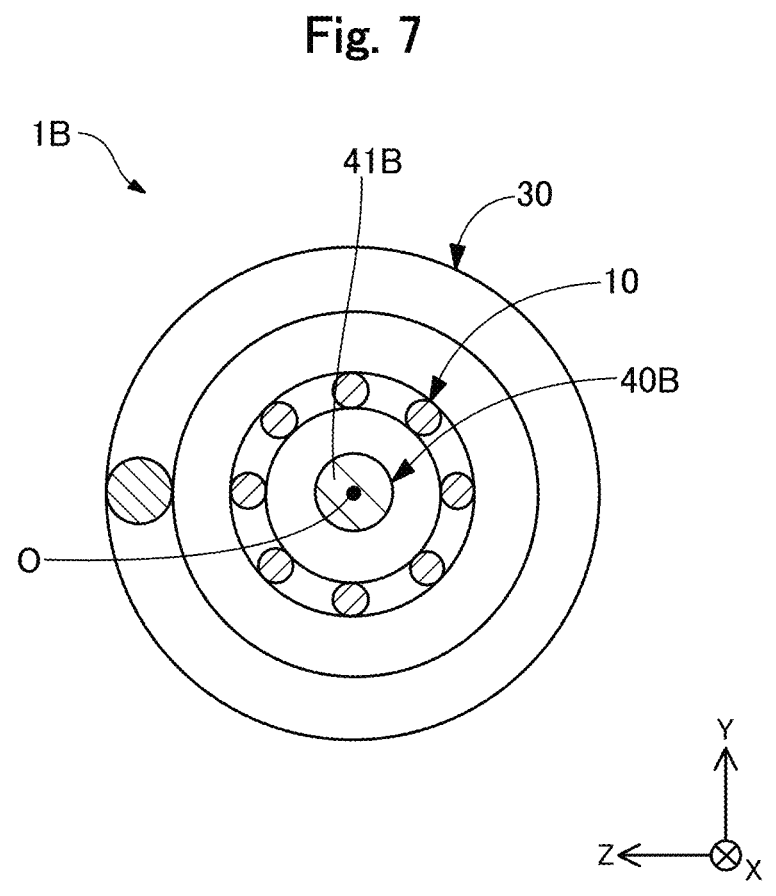

FIG. 7 is a diagram illustrating an example of a configuration of a guide wire 1B according to a third embodiment. FIG. 7 illustrates an example of a cross-sectional configuration along the line A-A in FIG. 2 in relation to the guide wire 1B of the third embodiment. The guide wire 1B of the third embodiment includes a core shaft 40B instead of the core shaft 40 in the configuration described in the first embodiment. The core shaft 40B includes a small-diameter portion 41B instead of the flat plate portion 41 described in the first embodiment. The small-diameter portion 41B is a portion having an approximately columnar shape in which the outer diameter is approximately constant from the proximal end to the distal end, and has an approximately circular cross-section as illustrated in FIG. 7. The outer diameter of the small-diameter portion 41B is identical to that of a portion of the tapered portion 42 having the smallest diameter.

As such, the configuration of the core shaft 40B can be modified in various ways, and the core shaft 40B may not have the flat plate portion 41 described in the first embodiment. In addition, the core shaft 40B may not have the small-diameter portion 41B described in the third embodiment, and the distal end of the tapered portion 42 may be fixed by the distal tip 61. The same effect as in the first embodiment described above can be provided also by this guide wire 1B of the third embodiment.

Fourth Embodiment

Figure 8:
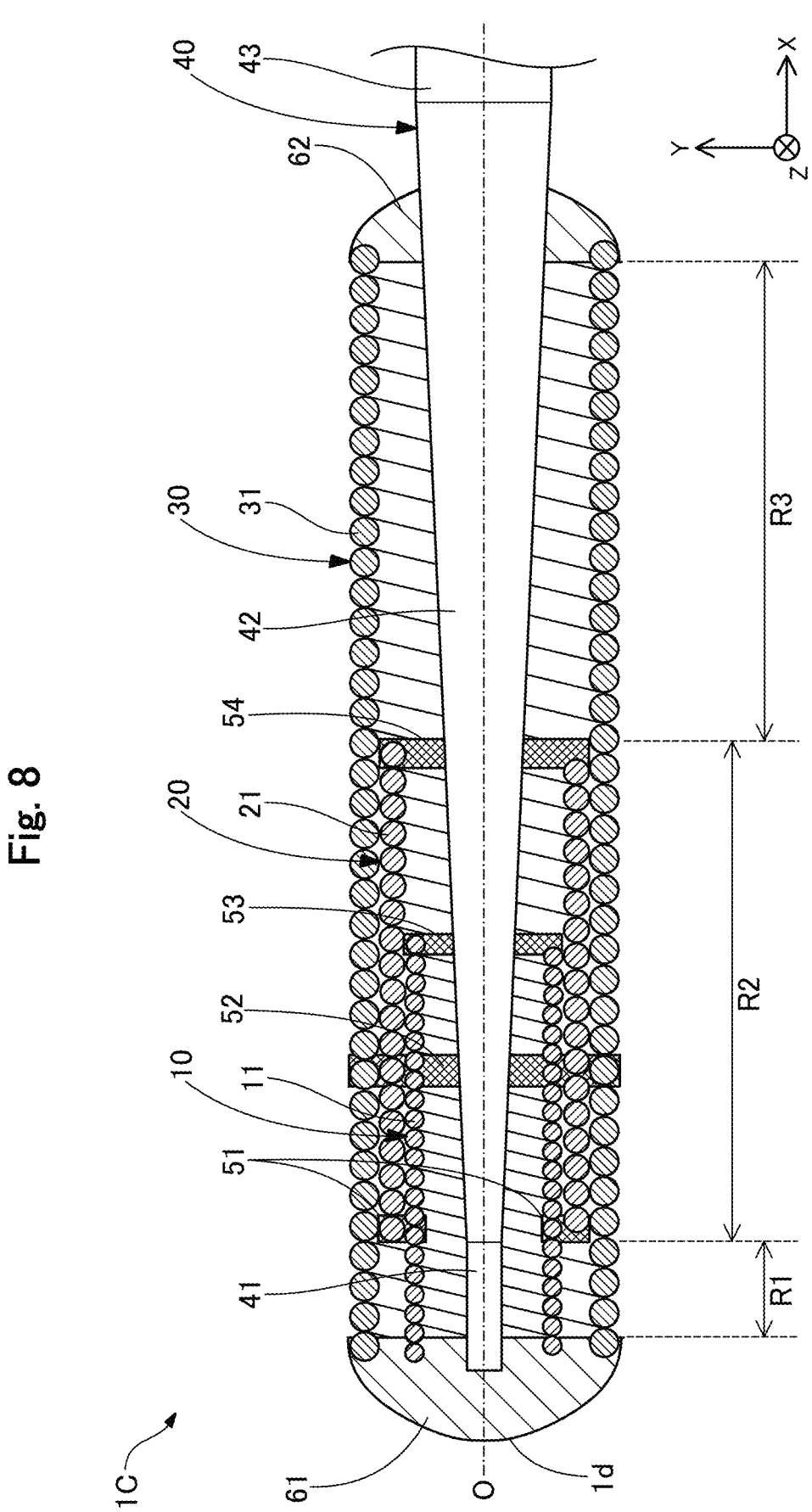
FIG. 8 is a diagram illustrating an example of a configuration of a guide wire according to a fourth embodiment.

FIG. 8 is a diagram illustrating an example of a configuration of a guide wire 1C according to a fourth embodiment. The guide wire 1C of the fourth embodiment further includes a second fixing portion 52 in addition to each component described in the first embodiment.

The second fixing portion 52 is disposed between the first fixing portion 51 and the third fixing portion 53 in the axis line O direction. In other words, the second fixing portion 52 is disposed at an arbitrary position on the more proximal end side than the distal end of the second coil body 20 and on the more distal end side than the proximal end of the first coil body 10. The second fixing portion 52 fixes a portion of the core shaft 40 (specifically, a portion of the tapered portion 42), a portion of the first coil body 10, a portion of the second coil body 20, and a portion of the third coil body 30, and integrally holds same. The second fixing portion 52 can be formed by means of an arbitrary bonding agent such as metal solder including silver solder, gold solder, zinc, Sn—Ag alloy, and Au—Sn alloy, or an adhesive including an epoxy-based adhesive, as with the distal tip 61 and the like.

As such, the configuration of the guide wire 1C can be modified in various ways, and the guide wire 1C may have a second fixing portion 52 fixing the core shaft 40 and the first to third coil bodies 10, 20, 30. The same effect as in the first embodiment described above can be provided also by this guide wire 1C of the fourth embodiment. In addition, according to the guide wire 1C of the fourth embodiment, since the second fixing portion 52 fixing a portion of the core shaft 40, a portion of the first coil body 10, a portion of the second coil body 20, and a portion of the third coil body 30 (tubular body) is provided, torquability of the guide wire 1C can be improved. In addition, since the first coil body 10, the second coil body 20, and the third coil body 30 are fixed to the core shaft 40 by the second fixing portion 52, the positions of the first coil body 10, the second coil body 20, and the third coil body 30 can be prevented from moving in the longitudinal direction (in other words, the first coil body 10, the second coil body 20, and the third coil body 30 can be prevented from displacing from one another).

Fifth Embodiment

Figure 9:
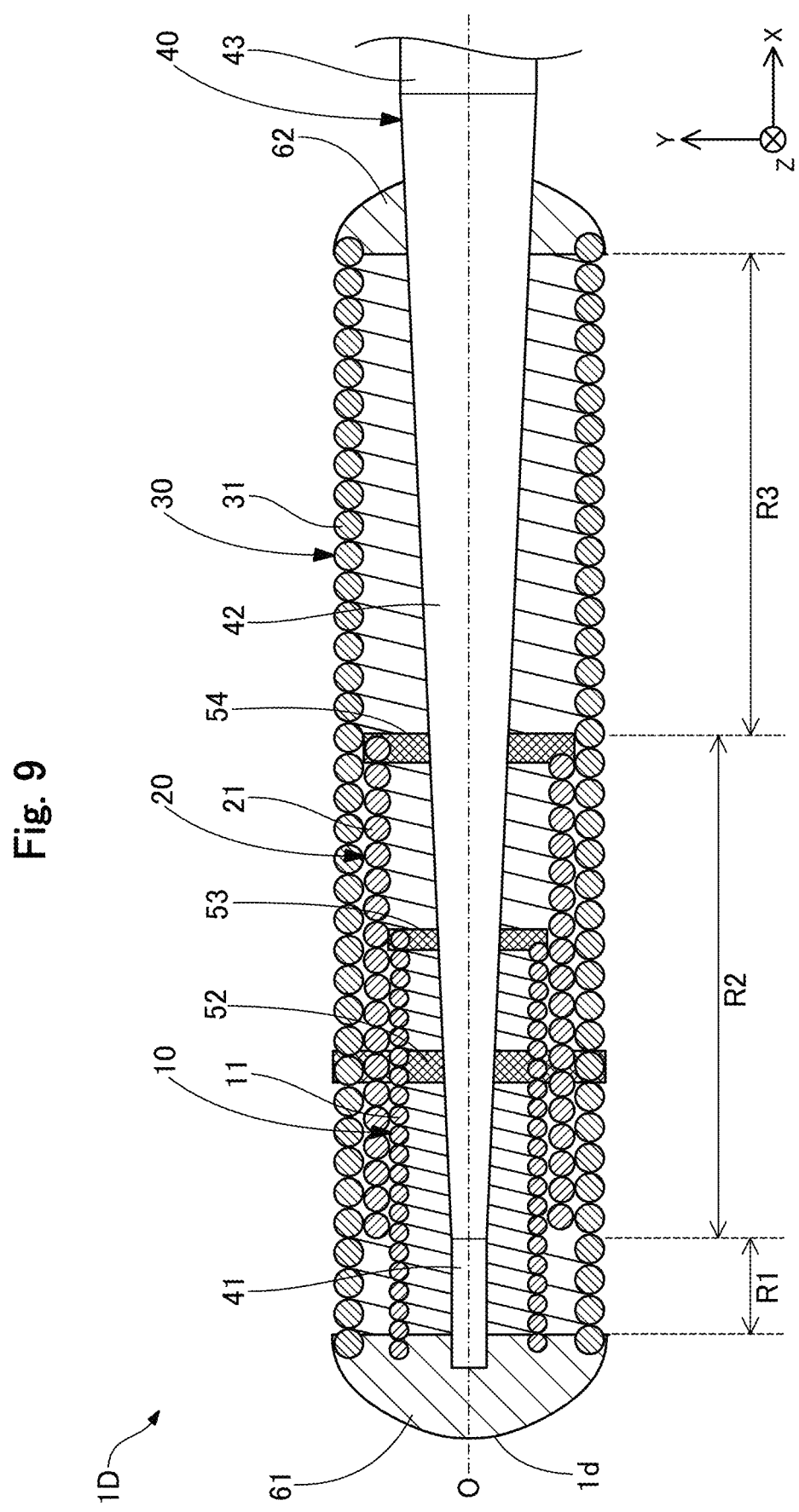
FIG. 9 is a diagram illustrating an example of a configuration of a guide wire according to a fifth embodiment.

FIG. 9 is a diagram illustrating an example of a configuration of a guide wire 1D according to a fifth embodiment. The guide wire 1D of the fifth embodiment does not include the first fixing portion 51 in the configuration described in the fourth embodiment. As such, the configuration of the guide wire 1D can be modified in various ways, and part of the fixing portions described above may be omitted. Although the first fixing portion 51 is omitted in the example illustrated in the drawing, the third fixing portion 53 and/or the fourth fixing portion 54 may be omitted instead of or in addition to the first fixing portion 51. The same effect as in the first and fourth embodiments described above can be provided also by this guide wire 1D of the fifth embodiment.

Sixth Embodiment

Figure 10:
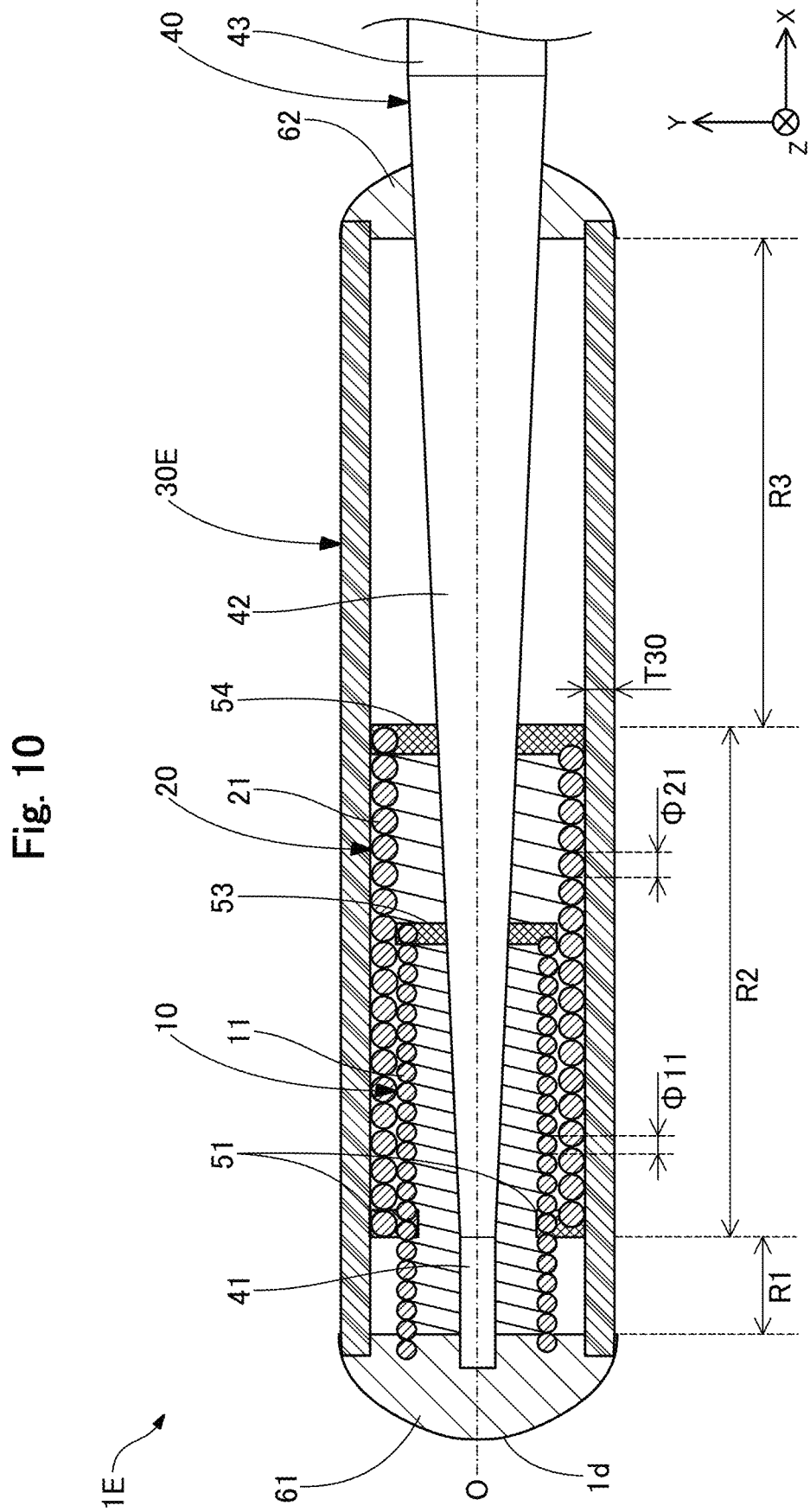
FIG. 10 is a diagram illustrating an example of a configuration of a guide wire according to a sixth embodiment.

FIG. 10 is a diagram illustrating an example of a configuration of a guide wire 1E according to a sixth embodiment. The guide wire 1E of the sixth embodiment includes a tube body 30E instead of the third coil body 30 in the configuration described in the first embodiment.

The tube body 30E is an approximately cylindrical member having openings on the distal end and the proximal end and having, in the inside thereof, an inner cavity communicating the both openings. The tube body 30E can be formed from an arbitrary resin material or an arbitrary metal material. The tube body 30E is disposed on the radially outer side of the second coil body 20 as with the third coil body 30 in the first embodiment, and surrounds a portion of the core shaft 40, the first coil body 10, and the second coil body 20. The distal end of the tube body 30E is fixed to the core shaft 40 and the first coil body 10 by the distal tip 61, and the proximal end of the tube body 30E is positioned on the more proximal end side than the proximal end of the second coil body 20 and is fixed to the core shaft 40 by the proximal end side fixing portion 62. In the present embodiment, the tube body 30E corresponds to the "tubular body".

As such, the configuration of the guide wire 1E can be modified in various ways, and the guide wire 1E may have a configuration in which the first coil body 10 and the second coil body 20 are covered using the tube body 30E instead of a coil body formed by winding a strand. Incidentally, from the viewpoint of maintaining the shape of the guide wire 1E on the distal end side, the thickness T30 of the tube body 30E may be larger than the outer diameter Ø11 of the strands 11 and may be larger than the outer diameter Ø21 of the strands 21. However, the thickness T30 of the tube body 30E may be smaller than at least one of the outer diameters Ø11 and Ø21. The same effect as in the first embodiment described above can be provided also by this guide wire 1E of the sixth embodiment. In addition, according to the guide wire 1E of the sixth embodiment, slidability of the guide wire 1E inside a blood vessel can be improved.

Seventh Embodiment

Figure 11:
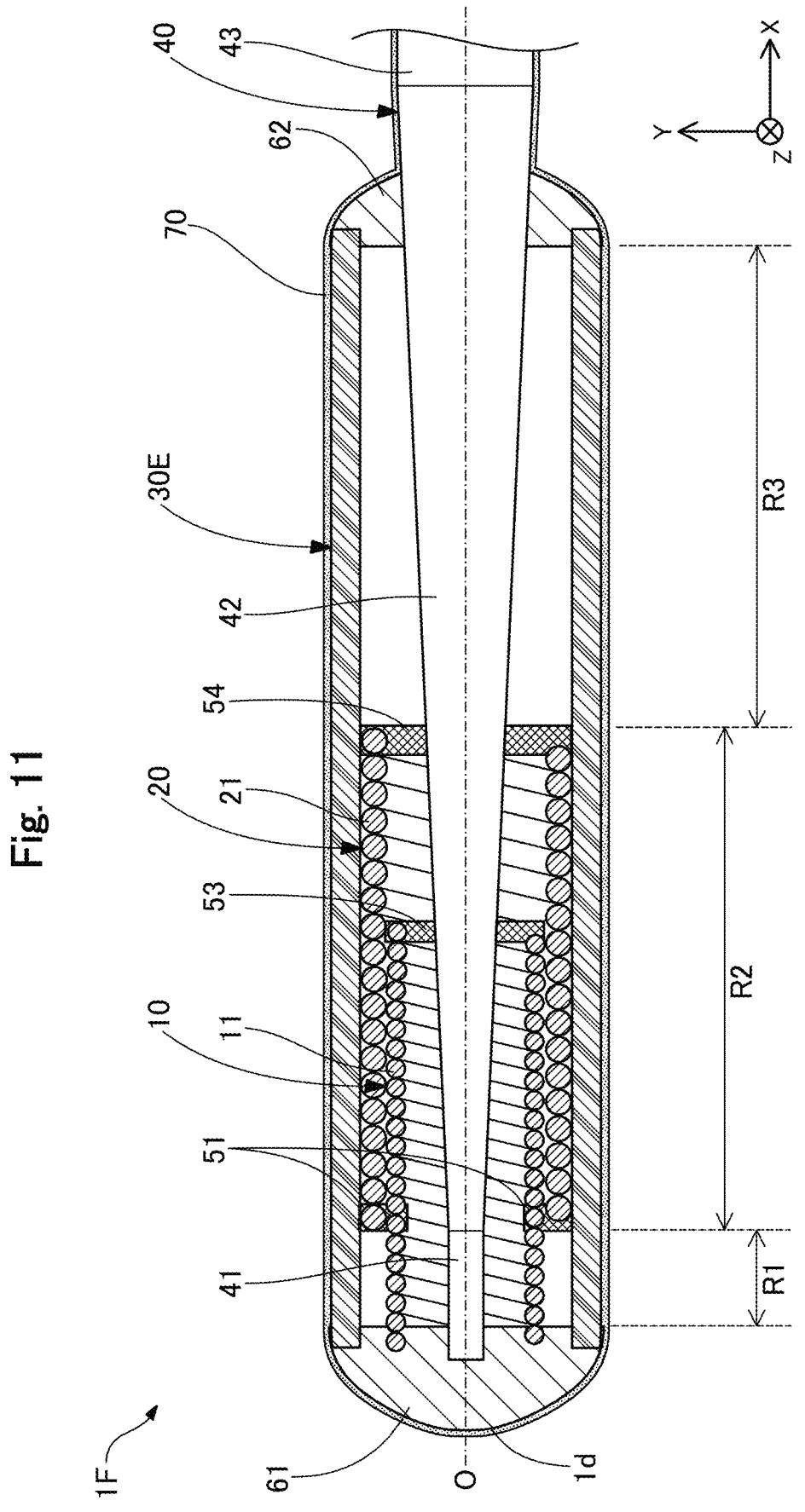
FIG. 11 is a diagram illustrating an example of a configuration of a guide wire according to a seventh embodiment.

FIG. 11 is a diagram illustrating an example of a configuration of a guide wire 1F according to a seventh embodiment. The guide wire 1F of the seventh embodiment further includes a coating layer 70 in the configuration described in the sixth embodiment. The coating layer 70 is a thin film coating the outer surface of the distal tip 61, the outer surface of the tube body 30E, the outer surface of the proximal end side fixing portion 62, and the outer surface of the core shaft 40 positioned on the more proximal end side than the proximal end side fixing portion 62. The coating layer 70 can be formed from a hydrophilic or hydrophobic resin, for example. The film thickness of the coating layer 70 can be arbitrarily determined.

As such, the configuration of the guide wire 1F can be modified in various ways, and the guide wire 1F may further include another component (for example, the coating layer 70) not described above. The same effect as in the first and sixth embodiments described above can be provided also by this guide wire 1F of the seventh embodiment. In addition, according to the guide wire 1F of the seventh embodiment, since the guide wire 1F includes the coating layer 70 coating the outer surfaces of the distal tip 61, the tube body 30E (tubular body), and the core shaft 40 positioned on the more proximal end side than the tube body 30E, slidability of the guide wire 1F inside a blood vessel can be further improved.

Eighth Embodiment

Figure 12:
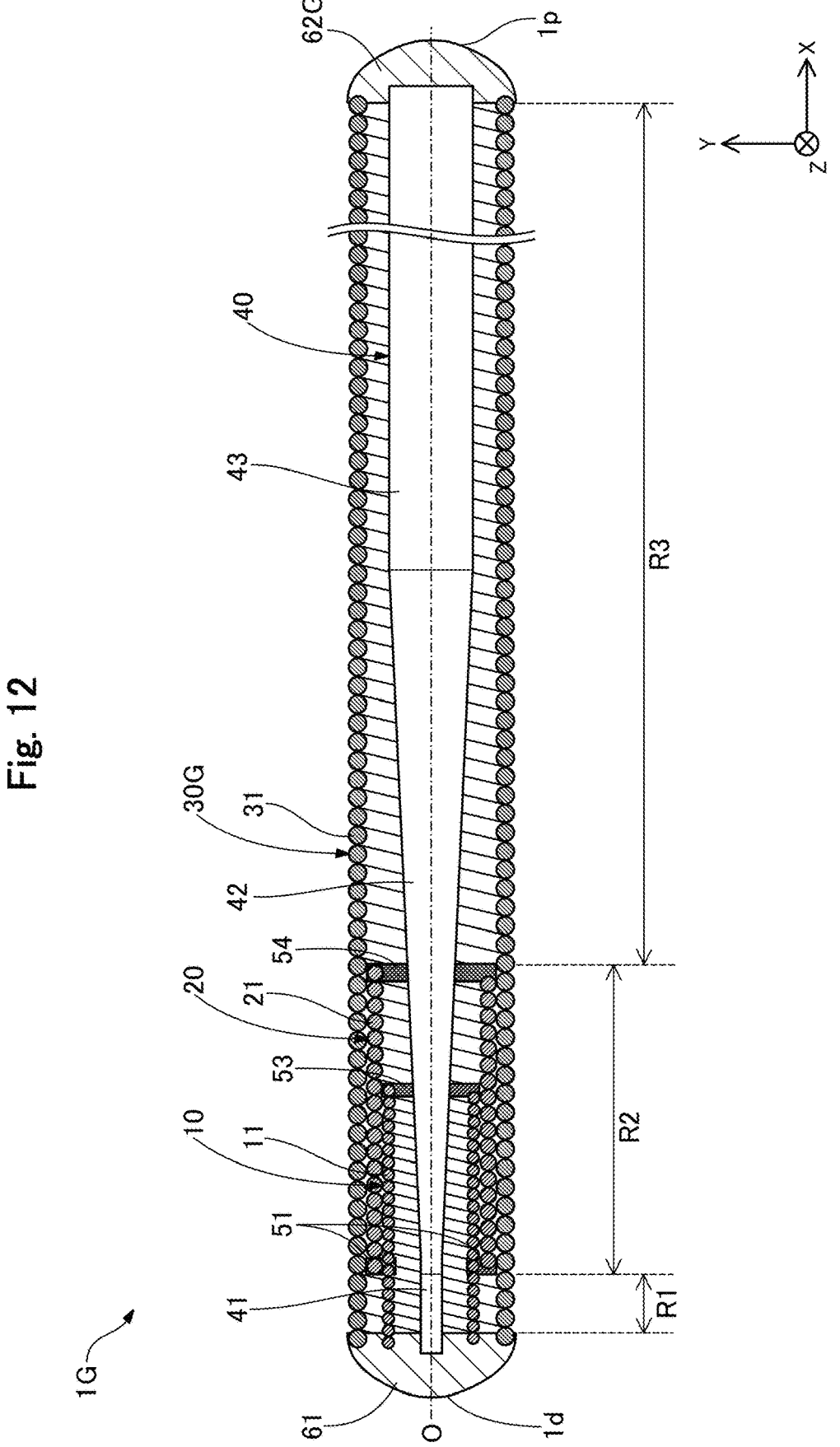
FIG. 12 is a diagram illustrating an example of a configuration of a guide wire according to an eighth embodiment.

FIG. 12 is a diagram illustrating an example of a configuration of a guide wire 1G according to an eighth embodiment. The guide wire 1G of the eighth embodiment includes a third coil body 30G instead of the third coil body 30 and includes a proximal end side fixing portion 62G instead of the proximal end side fixing portion 62 in the configuration described in the first embodiment.

The third coil body 30G surrounds the entire of the core shaft 40, the first coil body 10, and the second coil body 20. In the axis line O direction, the distal end of the third coil body 30G is located at the same position as the distal end of the first coil body 10, and the proximal end of the third coil body 30G is located at the same position as the proximal end of the core shaft 40. Incidentally, in the present embodiment, the term "identical" means being approximately identical and allows differences due to manufacturing errors and the like. The proximal end side fixing portion 62G is disposed at the proximal end of the third coil body 30G and integrally holds the proximal end of the third coil body 30G and the proximal end of the core shaft 40 (specifically, the proximal end of the large-diameter portion 43).

As such, the configuration of the guide wire 1G can be modified in various ways, and the guide wire 1G may have a configuration in which the entire of the core shaft 40 is surrounded by a tubular body (in the example illustrated in the drawing, the third coil body 30G). In addition, the guide wire 1G may further have a fixing portion fixing a portion of the third coil body 30G and a portion of the large-diameter portion 43. The same effect as in the first embodiment described above can be provided also by this guide wire 1G of the eighth embodiment. In addition, according to the guide wire 1G of the eighth embodiment, a guide wire 1G entirely covered with the tubular body can be provided.

Ninth Embodiment

Figure 13:
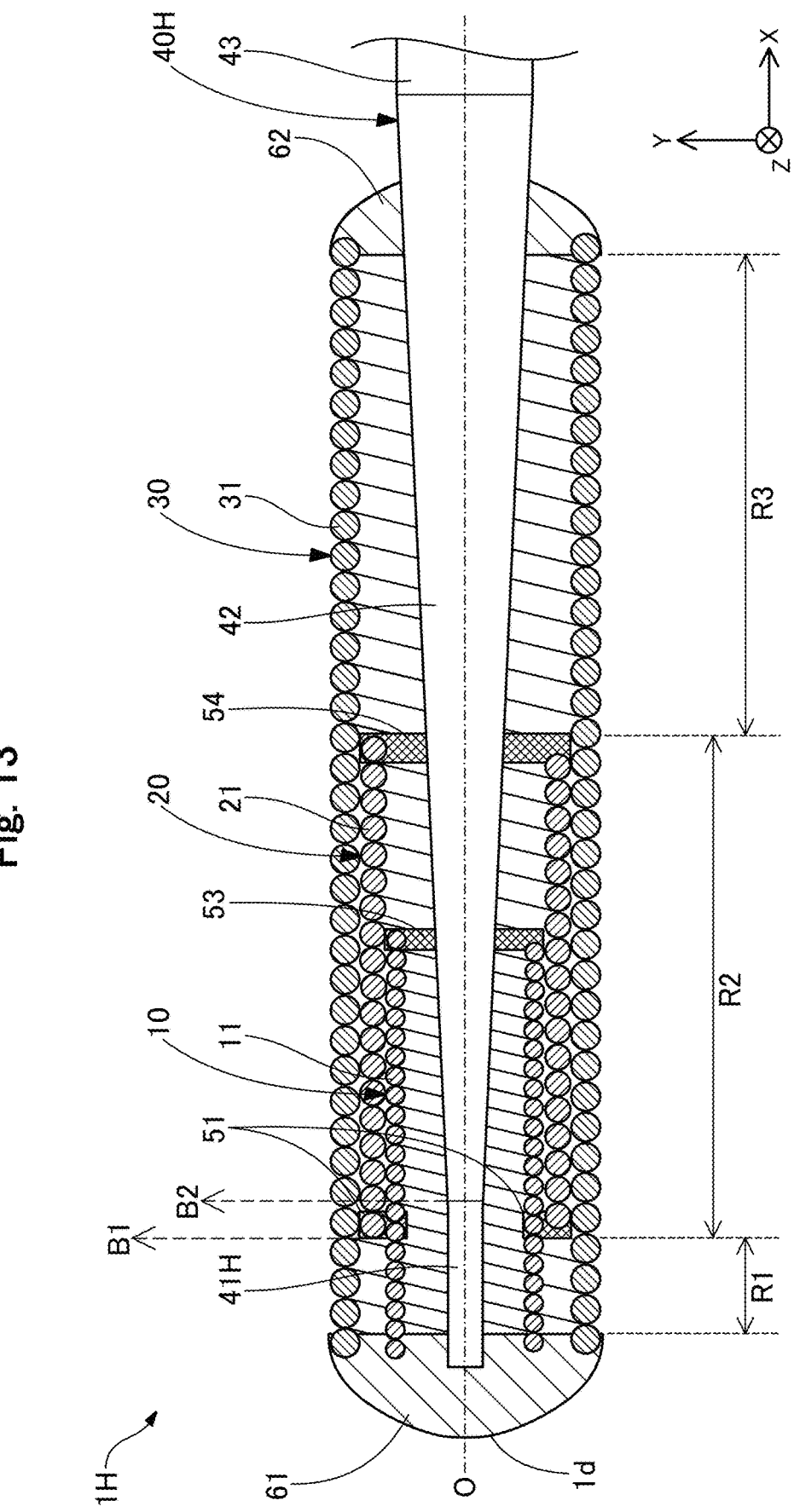
FIG. 13 is a diagram illustrating an example of a configuration of a guide wire according to a ninth embodiment.

FIG. 13 is a diagram illustrating an example of a configuration of a guide wire 1H according to a ninth embodiment. The guide wire 1H of the ninth embodiment includes a core shaft 40H instead of the core shaft 40 in the configuration described in the first embodiment. The core shaft 40H includes a flat plate portion 41H instead of the flat plate portion 41 described in the first embodiment. The flat plate portion 41H has a length in the axis line O direction (in other words, the longitudinal direction of the core shaft 40H) longer than that of the flat plate portion 41 described in the first embodiment. Therefore, the position B2 of the proximal end of the flat plate portion 41H is located on the more proximal end side than the position B1 of the distal end of the second coil body 20.

As such, the configuration of the core shaft 40H can be modified in various ways, and the position B2 of the proximal end of the flat plate portion 41H may not coincide with the position B1 of the distal end of the second coil body 20. Although, in the example illustrated in the drawing, the flat plate portion 41H longer than the flat plate portion 41 described in the first embodiment is illustrated, the length of the flat plate portion 41H may be shorter than that of the flat plate portion 41 described in the first embodiment. In this case, the position B2 of the proximal end of the flat plate portion 41H is located on the more distal end side than the position B1 of the distal end of the second coil body 20. The same effect as in the first embodiment described above can be provided also by this guide wire 1H of the ninth embodiment. In addition, according to the guide wire 1H of the ninth embodiment, the length of the portion serving as ribbon for imparting a shape can be freely changed.

Tenth Embodiment

Figure 14:
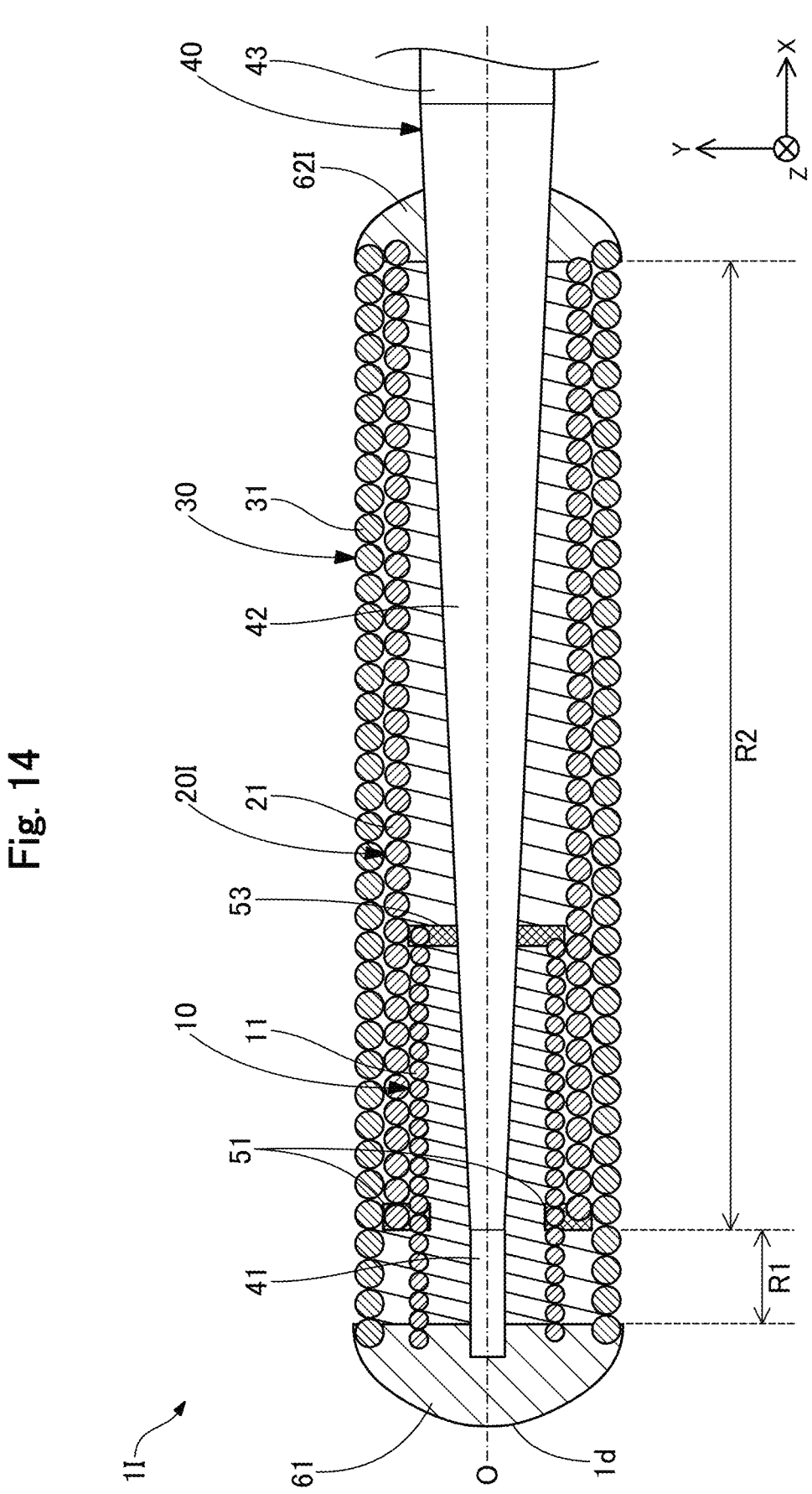
FIG. 14 is a diagram illustrating an example of a configuration of a guide wire according to a tenth embodiment.

FIG. 14 is a diagram illustrating an example of a configuration of a guide wire 1I according to a tenth embodiment. The guide wire 1I of the tenth embodiment includes a second coil body 20I instead of the second coil body 20, includes a proximal end side fixing portion 621 instead of the proximal end side fixing portion 62, and includes no fourth fixing portion 54 in the configuration described in the first embodiment.

In the axis line O direction, the distal end of the second coil body 20I is positioned between the distal end of the first coil body 10 and the proximal end of the first coil body 10, and the proximal end of the second coil body 20I is located at the same position as the proximal end of the third coil body 30. Incidentally, in the present embodiment, the term "identical" means being approximately identical and allows differences due to manufacturing errors and the like. The proximal end side fixing portion 621 is disposed at the proximal end of the third coil body 30 and integrally holds the proximal end of the third coil body 30, the proximal end of the second coil body 20I, and a portion of the core shaft 40. As illustrated in FIG. 14, the third region R3 in which the core shaft 40 is surrounded only by the third coil body 30 does not exist in the guide wire 1I of the tenth embodiment.

As such, the configuration of the guide wire 1I can be modified in various ways, and the proximal end of the second coil body 20I may be located at the same position as the proximal end of the third coil body 30, and the third region R3 may not exist. In addition, a fixing portion fixing a portion of the core shaft 40, a portion of the second coil body 20I, and a portion of the third coil body 30 may be further provided on the more proximal end side than the third fixing portion 53, in the guide wire 1I. The same effect as in the first embodiment described above can be provided also by this guide wire 1I of the tenth embodiment.

Eleventh Embodiment

Figure 15:
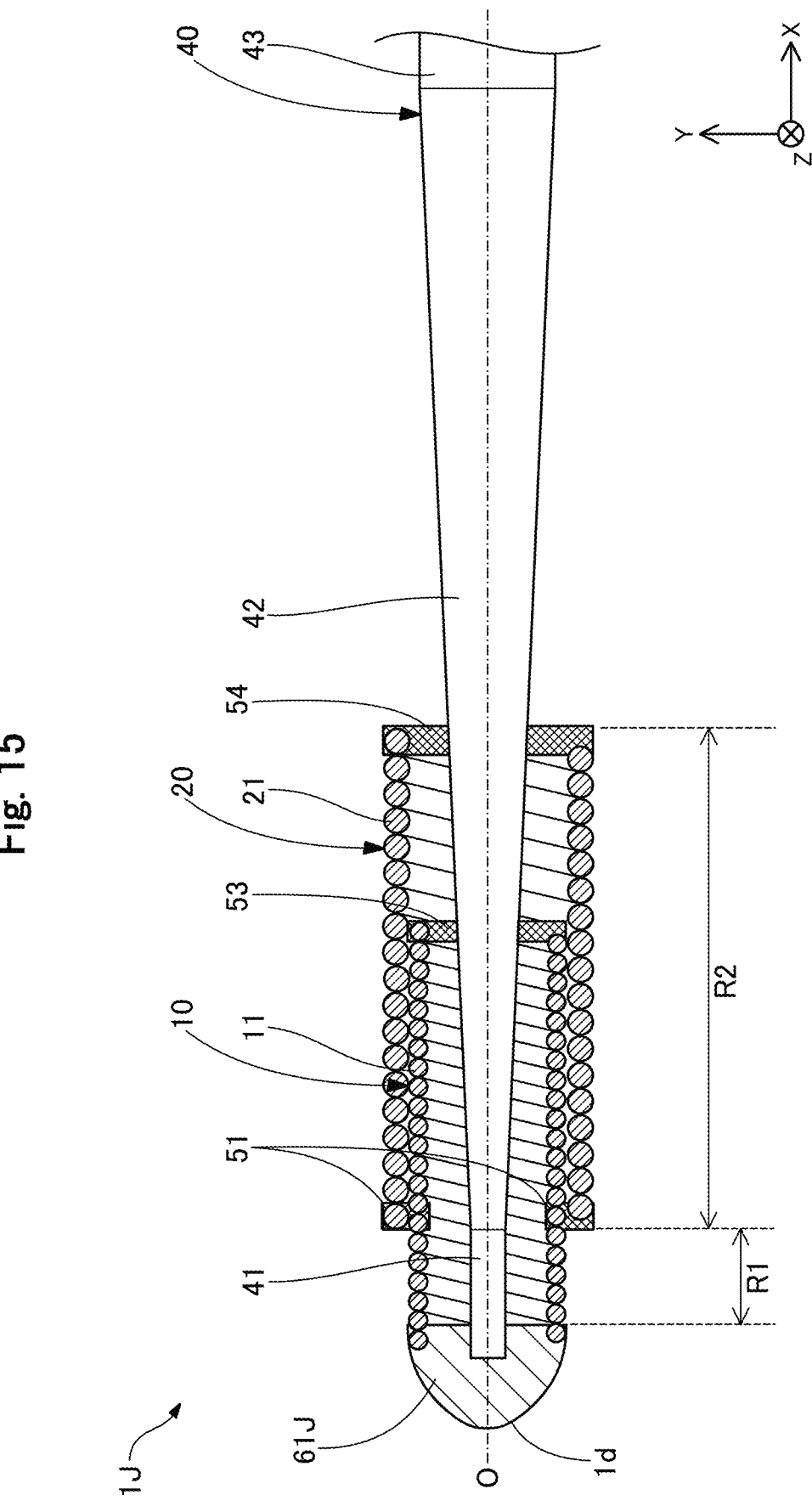
FIG. 15 is a diagram illustrating an example of a configuration of a guide wire according to an eleventh embodiment.

FIG. 15 is a diagram illustrating an example of a configuration of a guide wire 1J according to an eleventh embodiment. The guide wire 1J of the eleventh embodiment includes a distal tip 61J instead of the distal tip 61, and includes no third coil body 30 and no proximal end side fixing portion 62 described in the first embodiment, in the configuration described in the first embodiment.

Since the guide wire 1J includes no third coil body 30, a portion of the first coil body 10 on the distal end side and the second coil body 20 are not covered with the third coil body 30 and exposed. In addition, the guide wire 1J has the first region R1 and the second region R2 but has no third region R3 (region in which the core shaft 40 is surrounded by the third coil body 30). The distal tip 61J is disposed at the distal end of the first coil body 10 and integrally holds the distal end of the first coil body 10 and the distal end of the core shaft 40. Incidentally, the guide wire 1J may further have a hydrophilic or hydrophobic coating layer. In this case, the coating layer can be a thin film coating the outer surface of the distal tip 61J, the outer surface of a portion (FIG. 15: exposed portion) of the first coil body 10 on the distal end side, the outer surface of the second coil body 20, the outer surface of the first fixing portion 51, the outer surface of the fourth fixing portion 54, and the outer surface of the core shaft 40 positioned on the more proximal end side than the fourth fixing portion 54.

As such, the configuration of the guide wire 1J can be modified in various ways, and the guide wire 1J may have a configuration in which the third coil body 30 is omitted, and no third region R3 is provided. The same effect as in the first embodiment described above can be provided also by this guide wire 1J of the eleventh embodiment. In addition, according to the guide wire 1J of the eleventh embodiment, the guide wire 1J can be thinned, and the production man-hours and production costs for the guide wire 1J can be reduced by reducing the number of members constituting the guide wire 1J.

Variants of Embodiments

The disclosed embodiments are not limited to the embodiments described above and can be carried out in various aspects without departing from the spirit thereof, and the following modifications are also possible, for example.
Modification 1

An example of each of the configurations of guide wires 1 and 1A-1J is described in each of the first to eleventh embodiments above. However, the configuration of the guide wire 1 can be modified in various ways. For example, the core shaft 40 of the guide wire 1 may be provided with a small-diameter portion, a large-diameter portion, a flat portion, a tapered portion, or the like, as appropriate, according to performance required of the guide wire 1, and may not be provided with the flat plate portion 41 or the tapered portion 42 described above. For example, one or more of the first fixing portion 51, the second fixing portion 52, the third fixing portion 53, and the fourth fixing portion 54 may be omitted in the guide wire 1C.
Modification 2

An example of each of the configurations of the first to third coil bodies 10, 20, 20I, 30, and 30G and tube body 30E is described in each of the first to eleventh embodiments. However, these configurations can be modified in various ways. For example, an approximately cylindrical tube body may be used instead of the first coil body 10 and/or the second coil body 20. For example, at least one or more of the first coil body 10, the second coil body 20, and the third coil body 30 may be embedded in a thick wall portion of the approximately cylindrical tube body.
Modification 3

The configurations of the guide wires of first to eleventh embodiments and the configurations of the guide wires of the above-described variations 1 and 2 may be combined, as appropriate. For example, the guide wire 1 of each of the third to eleventh embodiments may include the first fixing portion 51A described in the second embodiment. For example, the guide wire 1 of each of the second and fourth to eleventh embodiments may include the small-diameter portion 41B described in the third embodiment. For example, the guide wire 1 of each of the second, third, and fifth to tenth embodiments may be provided with the second fixing portion 52 described in the fourth embodiment. For example, the guide wire 1 of each of the second to fifth and eighth to tenth embodiments may include the tube body 30E described in the sixth embodiment. For example, the guide wire 1 of each of the second to sixth and eighth to tenth embodiments may include the coating layer 70 described in the seventh embodiment. For example, the guide wire 1 of each of the second to seventh, ninth, and tenth embodiments may include the third coil body 30G described in the eighth embodiment.

Hereinbefore, the present mode has been described on the basis of the embodiments and variations; however, the above-described forms for carrying out the mode are intended to facilitate understanding of the present mode and are not intended to limit the present mode. In some instances, as would be apparent to one of skill in the art as of the filing of the present application, features, character- istics, and/or elements described in connection with a par- ticular embodiment may be used singly or in combination with features, characteristics, and/or elements described in connection with other embodiments unless otherwise indi- cated. The present mode can be changed or modified without departing from the spirit thereof and the scope of claims, and the present mode also encompasses equivalents thereof. In addition, technical features thereof can be omitted, as appro- priate, unless they are described as essential in the present specification.

No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

DESCRIPTION OF REFERENCE NUMERALS

1,1A-1J . . . Guide wire
2 . . . Measuring device
3 . . . Load sensor
4 . . . Gripping tool
5 . . . Measuring object
10 . . . First coil body
11 . . . Strand
20,20I . . . Second coil body
21 . . . Strand
30,30G . . . Third coil body
30E . . . Tube body
31 . . . Strand
40,40B,40H . . . Core shaft
41,41H . . . Flat plate portion
41B . . . Small-diameter portion
42 . . . Tapered portion
43 . . . Large-diameter portion
51,51A . . . First fixing portion
52 . . . Second fixing portion
53 . . . Third fixing portion
54 . . . Fourth fixing portion
61,61J . . . Distal tip
62,62G,621 . . . Proximal end side fixing portion
70 . . . Coating layer

What is claimed is:

1. A guide wire comprising:
   a core shaft having an elongated outer shape;
   a first coil body disposed to surround a distal end portion of the core shaft;
   a second coil body disposed radially outside from the first coil body;
   a tubular body disposed radially outside from the second coil body;
   a distal tip fixing a distal end of the core shaft and a distal end of the first coil body and a distal end of the tubular body; and
   a second fixing portion integrally fixing a portion of the core shaft, a portion of the first coil body, a portion of the second coil body, and a portion of the tubular body, wherein
   in a longitudinal direction of the core shaft, a distal end of the second coil body is between the distal end of the first coil body and a proximal end of the first coil body, and a proximal end of the second coil body is on a more proximal end side than the proximal end of the first coil body, and
   bending stiffness of the first coil body is smaller than bending stiffness of the second coil body,
   wherein the core shaft includes a tapered portion in which an outer diameter decreases from a proximal end to a distal end, and a flat plate portion on a more distal end side than the tapered portion and has a flat plate outer shape; and
   a proximal end of the flat plate portion is aligned with the distal end of the second coil body in a longitudinal direction of the core shaft.

2. The guide wire according to claim 1, further comprising a first fixing portion fixing a distal end portion of the second coil body and a portion of the first coil body.

3. The guide wire according to claim 2, wherein the first fixing portion further fixes the distal end portion of the second coil body and a portion of the core shaft.

4. The guide wire according to claim 1, wherein
   a proximal end of the tubular body is on a more proximal end side than the proximal end of the second coil body.

5. The guide wire according to claim 4, further compris- ing:
   a coating layer coating outer surfaces of the distal tip, the tubular body, and the core shaft extending from a more proximal end side than the tubular body.

6. The guide wire according to claim 1, further comprising a third fixing portion fixing a proximal end portion of the second coil body and a second portion of the core shaft on a more proximal end side than the first portion of the core shaft.

7. The guide wire according to claim 2, further comprising a third fixing portion between the first fixing portion and the second fixing portion that fixes a portion of the second coil body, a portion of the first coil body, and a second portion of the core shaft on a more proximal end side than the first portion of the core shaft.

8. The guide wire according to claim 1, further compris- ing:
   a third coil body disposed radially outside from the second coil body; and
   the distal tip further fixes a distal end of the third coil body.

9. The guide wire according to claim 8, wherein in the longitudinal direction of the core shaft, a proximal end of the third coil body is on a more proximal end side than the proximal end of the second coil body.

10. The guide wire according to claim 9, further comprising a proximal end side fixing portion that fixes the third coil body to a portion of the core shaft.

11. The guide wire according to claim 10, wherein the core shaft includes a tapered portion in which an outer diameter decreases from a proximal end to a distal end, and a large diameter portion on a most proximal end side of the core shaft, wherein the proximal end side fixing portion fixes the third coil body to a portion of the tapered portion.

12. The guide wire according to claim 10, wherein the core shaft includes a tapered portion in which an outer diameter decreases from a proximal end to a distal end, and a large diameter portion on a most proximal end side of the core shaft, wherein the proximal end side fixing portion fixes the third coil body to a portion of the large diameter portion.

13. The guide wire according to claim 12, wherein the proximal end side fixing portion fixes the third coil body to a proximal end of the large diameter portion.

14. The guide wire according to claim 1, wherein a proximal end of the tubular body is on a more proximal end side than the proximal end of the second coil body.

15. The guide wire according to claim 14, further comprising a fixing portion fixing a portion of the core shaft, a portion of the first coil body, a portion of the second coil body, and a portion of the tubular body.

16. The guide wire according to claim 15, further comprising a coating layer coating outer surfaces of the distal tip, the tubular body, and the core shaft extending from a more proximal end side than the tubular body.

17. A guide wire comprising:

a core shaft having an elongated outer shape;

a first coil body disposed to surround a distal end portion of the core shaft;

a second coil body disposed radially outside from the first coil body;

a tubular body disposed radially outside from the second coil body; and a distal tip fixing a distal end of the core shaft and a distal end of the first coil body, and further fixing a distal end of the tubular body, wherein in a longitudinal direction of the core shaft, a distal end of the second coil body is between the distal end of the first coil body and a proximal end of the first coil body, and a proximal end of the second coil body is on a more proximal end side than the proximal end of the first coil body, and bending stiffness of the first coil body is smaller than bending stiffness of the second coil body, and the core shaft includes a tapered portion in which an outer diameter decreases from a proximal end to a distal end, and a flat plate portion on a more distal end side than the tapered portion and having a flat plate outer shape, and in a longitudinal direction of the core shaft, the second coil body is disposed at a position not overlapping with the flat plate portion.

* * * * *